United States Patent [19]

Soper

[11] 4,376,388

[45] Mar. 15, 1983

[54] SHOCK SIMULATOR

[75] Inventor: William G. Soper, King George, Va.

[73] Assignee: The United States of America as represented by the Secretary of the Navy, Washington, D.C.

[21] Appl. No.: 242,199

[22] Filed: Mar. 10, 1981

[51] Int. Cl.$^3$ .................. G01N 19/00; G01N 3/30
[52] U.S. Cl. ............................. 73/12; 73/167
[58] Field of Search ............................. 73/12

[56] References Cited

U.S. PATENT DOCUMENTS

| | | | |
|---|---|---|---|
| 3,226,974 | 1/1966 | Bresk et al. | 73/12 |
| 3,352,143 | 11/1967 | Bollar | 73/11 |
| 3,693,432 | 9/1972 | Stewart et al. | 73/12 |
| 3,927,554 | 12/1975 | Langhorst | 73/11 |
| 4,004,794 | 1/1977 | Jarret et al. | 188/268 |

*Primary Examiner*—S. Clement Swisher

*Attorney, Agent, or Firm*—R. F. Beers; K. E. Walden; W. R. Henderson

[57] ABSTRACT

A projectile ground shock simulator for simulating the force pulse on a projectile in testing for shock effect on the guidance system of the projectile. The simulator incorporates a liquid/solid material as an energy absorbing and storing spring for simulating the force pulse on the projectile. The projectile is positioned in a drop tube and impacted with a drop vehicle to simulate the forces created during firing of the projectile. The drop vehicle is provided with the liquid/solid spring having a piston and cylinder on the impact face of the drop vehicle. The cylinder is filled with a liquid or solid polymer material having a high bulk modulus of compressibility which gives the spring volumetric stiffness. The spring thus duplicates the force pulse acting on a fired projectile and also allows for the drop vehicle to be reused.

10 Claims, 3 Drawing Figures

SHOCK SIMULATOR

BACKGROUND OF THE INVENTION

The present invention relates to a shock simulator and more particularly to a simulator for simulating the force pulse on a fired projectile.

Previously, the methods used for testing projectiles required impacting the projectile with a block of ductile metal such as lead or soft aluminum. The use of a soft deformable metal created the desired force pulse similar to that created by firing the projectile. The disadvantage in using this type of a simulator is that the metal is not resilient and, upon release of the force load, the metal does not resume its original dimensions. As a consequence, the block of ductile deformed metal must be replaced after every use of the simulator. Deformation of the metal block also results in a dissipation of energy thus detracting from the force pulse. The shock simulator of the present invention, in contrast to the prior methods, releases virtually all of the stored energy without deformation of metal and subsequent energy loss and thus can be reused after each simulation without replacement of parts.

SUMMARY OF THE INVENTION

Accordingly, there is provided in the present invention a shock simulator for simulating the force pulse on a projectile in testing for shock effect on the guidance system or other hardware of the projectile.

The simulator incorporates a liquid or solid spring for simulating the force pulse on a projectile during firing of the projectile. The simulator is provided with a drop tube or tower in which the projectile is positioned. A drop vehicle is positioned in the tube or tower above the projectile so as to impact on the projectile when released and subjected to gravitational force. The drop vehicle simulates the force created during firing of the projectile.

The drop vehicle is provided with a liquid or solid spring having a cylinder and piston which are positioned on the impact face of the drop vehicle. A chamber is formed by the piston and cylinder and an energy absorbing and storing material is positioned in the chamber. The energy storing material is a liquid or solid material having a high bulk modulus which gives the spring volumetric stiffness. The spring duplicates the force pulse acting on a fired projectile by reducing the volume of both the chamber and the energy absorbing material upon impact creating equal hydrostatic pressure in all directions. The volume of the chamber and energy absorbing material returns to normal upon the release of the force pulse.

OBJECTS OF THE INVENTION

It is an object of the present invention to provide a shock simulator for simulating the force pulse on a fired projectile.

It is another object of the present invention to provide a shock simulator with a stiff elastic member for absorbing and storing energy.

It is a further object of the present invention to provide a shock simulator which can be reused without the replacement of parts.

It is still a further object of the present invention to provide a shock simulator in which the force resisting compression is proportional to the amount of compressive force.

Other objectives, advantages, and novel features of the present invention will become apparent from the following detailed description of the invention when considered in conjunction with the drawings.

BRIEF DESCRIPTION OF THE DRAWINGS

A more complete appreciation of the invention and many of the attendant advantages thereof will be readily understood by reference to the following detailed description when considered with the accompanying drawings in which like reference numerals refer to like parts throughout the figures and wherein.

DESCRIPTION OF THE PREFERRED EMBODIMENT

Figure 1:
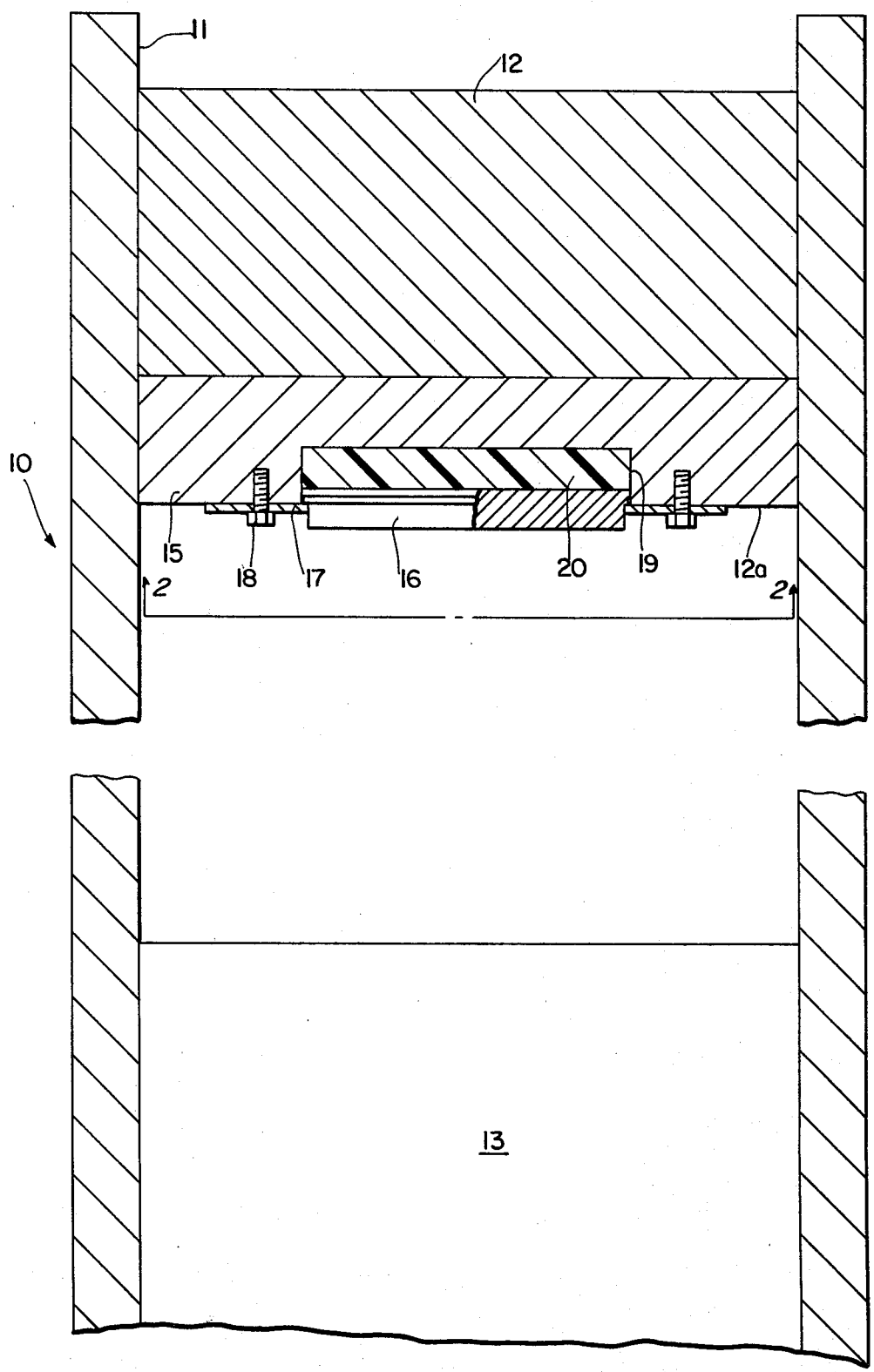
FIG. 1 illustrates in cross section a side view of the simulator of the present invention.

Referring to FIG. 1, there is illustrated in cross section a side view of the shock simulator 10 of the present invention. The simulator is provided with a cylindrical drop tube or tower 11. Positioned in the drop tower is a drop vehicle 12 which is positioned so as to impact on projectile 13. The projectile and drop vehicle are positioned so as to utilize gravitational force to drive the drop vehicle into the projectile. It is contemplated that other means may be used to propel the drop vehicle into the projectile.

The drop vehicle is provided with an impact face 12a on which is mounted a liquid or solid spring for producing a force pulse on the projectile similar to the pulse created by firing the projectile.

The spring is provided with a cylinder 15 in which is mounted piston 16 so as to form chamber 19. The piston and cylinder are made of a high strength material such as steel so as to withstand the large forces generated during operation of the simulator.

An energy absorbing and storing material 20 is positioned in chamber 19 such that when a force is applied to piston 16 material 20 is compressed to allow a piston displacement that is approximately proportional to the force applied. When the force is removed, the energy absorbing material returns to its original volume and the piston returns to its original position.

Figure 2:
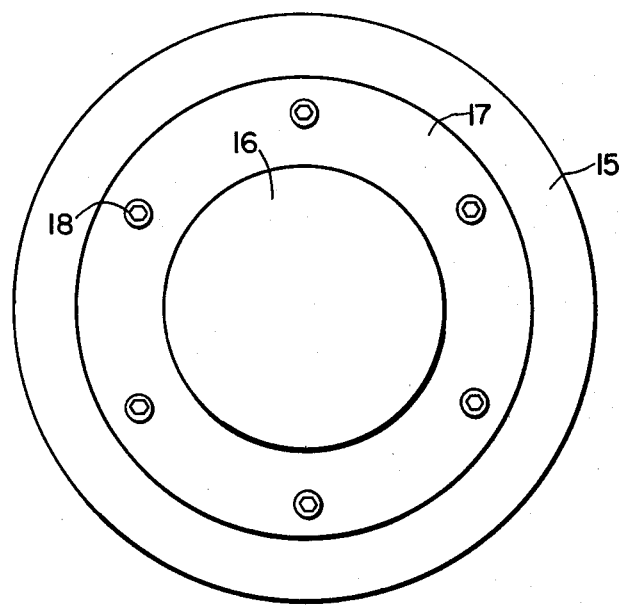
FIG. 2 illustrates a bottom view of the liquid or solid spring taken along line 2—2 of FIG. 1.

As shown in FIGS. 1 and 2, piston 16 is held in cylinder 15 by means of retainer ring 17 and threaded fasteners 18. It is contemplated that any equivalent means may be utilized for retaining piston 16 in cylinder 15.

As illustrated in FIG. 1, piston 16 is configured so as to have a piston diameter which fits closely with the diameter of cylinder 15. This effectively seals the energy absorbing and storing material in cylinder 15. Piston 16 is also provided with a narrow diameter on the piston face which impacts on the projectile. This narrower diameter permits the piston to tilt slightly on impact without binding in the cylinder. The walls of cylinder 15 are constructed with an added thickness to enable the cylinder to withstand the forces generated upon impact with the projectile.

Figure 3:
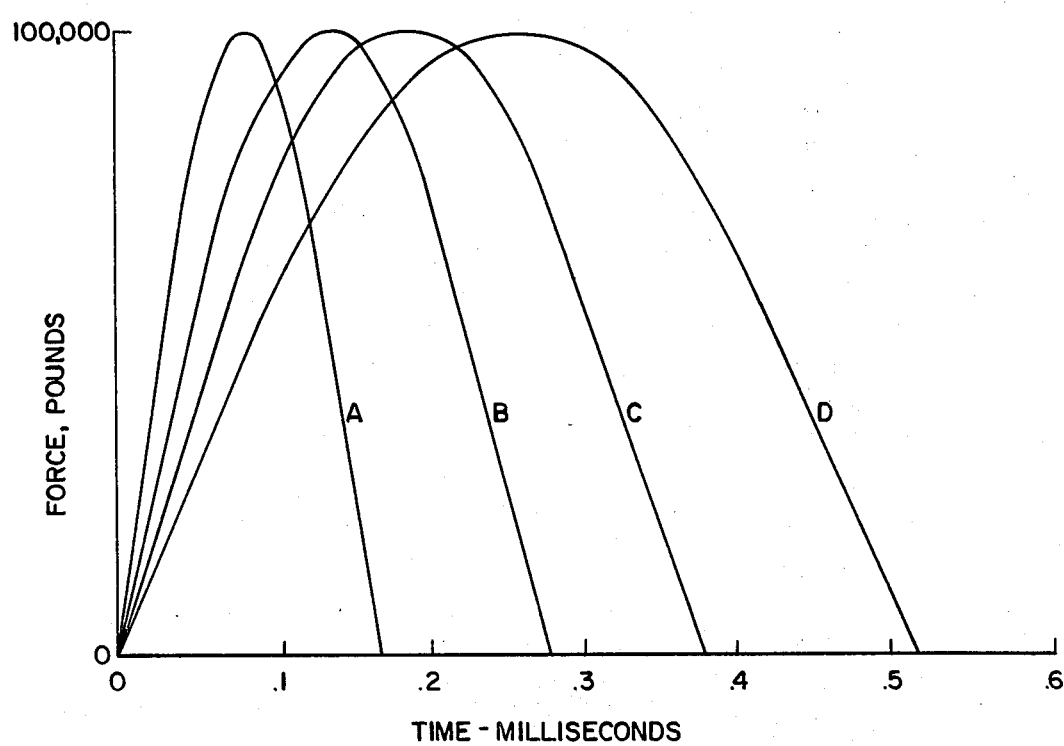
FIG. 3 illustrates force pulse curves for various materials.

The disclosed simulator can be used wherever a compact, high stiffness spring is desired. Referring to FIG. 3 there is illustrated various force pulse curves for the compressible materials listed in Table I.

TABLE I

| Curve | Material | Bulk Modulus, $10^6$ p.s.i | Impact Velocity Required, ft/sec |
|---|---|---|---|
| A | melamine formaldehyde | 2.60 | 5.7 |
| B | Nylon | 0.91 | 9.7 |
| C | water | 0.51 | 13.0 |
| D | diethyl ether | 0.27 | 17.8 |

As shown in FIG. 3, a material such as melamine formaldehyde, curve A, with a high bulk modulus, produces a force pulse of short duration and requires lower velocity for a given pulse intensity than a material with a low bulk modulus such as diethyl ether, shown as curve D.

Pulse duration is given by:

$$PD = \pi \frac{\sqrt{ml}}{BA}$$

where:
m = mass of the drop vehicle
l = thickness of compressible material
B = bulk modulus of material
A = area of the piston The above relationship indicates that four parameters are available for adjusting the pulse duration. Increasing either the area of the piston or the bulk modulus will decrease the pulse duration while increasing the mass of the drop vehicle or the thickness of material 20 will increase the pulse duration.

Pulse intensity is given by:

$$PI = V \frac{\sqrt{BA}}{l} m$$

where V = impact velocity of the drop vehicle. This relationship indicates that five parameters are available for adjusting the pulse intensity. Increasing the drop vehicle velocity or mass, piston area or bulk modulus will result in an increase in the pulse intensity while increasing the thickness of material 20 will result in a decrease in pulse intensity.

In addition to the materials listed in Table I, energy absorbing and storing material 20 can be any compressible liquid or solid material such as grease, polyethylene, silicone rubber or neoprene.

It is thus apparent that the disclosed projectile shock simulator provides a means for simulating the force pulses on a projectile during firing of the projectile. The disclosed simulator produces a force pulse similar to the projectile firing pulse and is reusable indefinitely without replacement of parts.

Many obvious modifications and embodiments of the specific invention other than those set forth above will readily come to mind to one skilled in the art having the benefit of the teachings presented in the foregoing description and the accompanying drawings of the subject invention and hence it is to be understood that such modifications are included within the scope of the appended claims.

What is claimed as new and desired to be secured by Letters Patent of the United States is:

1. A device for simulating a shock pulse on a projectile, comprising:
   means for stationarily positioning the projectile to receive a direct impact;
   means for directly impacting the projectile, and means for directly impacting mounted in spaced apart relationship with the projectile; and
   means for producing a shock pulse on the projectile from the direct impact thereon, said means for producing the shock pulse mounted to said means for directly impacting and positioned between said means for directly impacting and the projectile.

2. The device of claim 1 wherein the means for stationarily positioning the projectile comprises a tower, said projectile being stationarily positioned at a first end of the tower and said means for impacting being positioned at the opposite end of the tower defining the spaced apart relationship between the projectile to be impacted and said means for impacting.

3. The device of claim 1 wherein the means for stationarily positioning the projectile comprises a cylinder, said projectile being stationarily positioned at a first end of the cylinder and said means for impacting being positioned at the opposite end of the cylinder defining the spaced apart relationship between the projectile to be impacted and said means for impacting.

4. The device of claim 1 wherein the means for producing a shock pulse from the direct impact with the projectile comprises:
   a cylinder and piston forming a chamber mounted on a drop vehicle; and
   an energy storing and absorbing material in the chamber, said chamber and material decreasing in volume and having an equal hydrostatic force in all directions upon direct impact with the projectile and returning to the original volume after impact.

5. A device for simulating a shock pulse on a projectile, comprising:
   means for stationarily positioning the projectile for direct impact thereon;
   means for directly impacting the projectile, and means for directly impacting mounted spaced apart from the projectile;
   means for producing a shock pulse on the projectile from the direct impact thereon, said means for producing the shock pulse mounted to said means for directly impacting and positioned between said means for directly impacting and the projectile comprising:
   a cylinder and piston forming a chamber mounted on a drop vehicle; and
   an energy storing and absorbing material in the chamber, said chamber and material decreasing in volume and having an equal hydrostatic force in all directions upon impact with the projectile and returning to the original volume after impact.

6. The device of claim 4 wherein the material is solid.

7. The device of claim 4 wherein the material is liquid.

8. The device of claims 4 or 5 wherein the material has a high bulk modulus of compressibility.

9. The device of claim 5 wherein the material is solid.

10. The device of claim 5 wherein the material is liquid.

* * * * *